United States Patent [19]

Looney et al.

[11] Patent Number: 4,999,294
[45] Date of Patent: Mar. 12, 1991

[54] METHOD FOR PRODUCING THE FOKI RESTRICTION ENDONUCLEASE AND METHYLASE

[75] Inventors: Mary E. C. Looney, Beverly; Geoffrey G. Wilson, Boxford, both of Mass.

[73] Assignee: New England Biolabs, Inc., Beverly, Mass.

[21] Appl. No.: 134,236

[22] Filed: Dec. 17, 1987

[51] Int. Cl.[5] .................. C12N 15/52; C12N 9/22; C12N 1/21
[52] U.S. Cl. ........................... 435/172.3; 435/199; 435/252.33; 435/320.1; 536/27; 935/29; 935/73; 935/80
[58] Field of Search ..................... 435/172.3, 199, 320, 435/252.3, 252.33; 935/29, 73, 80, 82; 536/27

[56] References Cited

FOREIGN PATENT DOCUMENTS 0193413 3/1986 European Pat. Off. .
0248678 9/1987 European Pat. Off. .

OTHER PUBLICATIONS

Wilson, G. G. (1988), Trends in Genetics 4(11), 314–318.
Lunnen, K. D., et al. (1988) Gene 74, 25–32.
Wilson, G. G. (1988) Gene 74, 281–289.
Greene, P. J. et al. (1981), J. Biol. Chem. 256 (5), 2143–2153.
Newman, A. K., et al. (1981), J. Biol. Chem. 256(5), 2131–2139.
Schoner, B., et al. (1983), Gene 24, 227–236.
Walder, R. Y., et al. (1984), J. Biol. Chem. 259(12), 8015–8026.
Mann et al., Gene 3:97–112 (1978).
Kosykh et al., Molec. Gen. Genet. 178:717–718 (1980).
Walder et al., Proc. Nat. Acad. Sci. U.S.A. 78, 1503–1507 (1981).
Bougueleret et al., Nucleic Acids Res. 12:3659–3676 (1984).
Gingeras and Brooks, Proc. Natl. Acad. Sci. U.S.A. 80:402–406 (1983).
Theriault and Roy, Gene 19:355–359 (1982).
Blumenthal et al., J. Bacteriol. 164:501–509 (1985).
Kiss et al., Nucleic Acids Res. 13:6403–6421 (1985).
Szomolanyi et al., Gene 10:219–225, (1980).
Janulaitis et al., Gene 20:197–204 (1982).
Kiss and Baldauf, Gene 21:111–119, (1983).
Walder et al., J. Biol. Chem. 258:1235–1241 (1983).
Raleigh and Wilson, Proc. Natl. Acad. Sci. U.S.A. 83:9070–9074 (1986).
Sugisaki and Kanazawa, Gene 16:73–78 (1981).
Birnboin and Doly, Nucleic Acids Res. 7:1513 (1979).
Nwankwo and Wilson, Mol Gen Genet 290:570–574 (1987).

*Primary Examiner*—Elizabeth C. Weimar
*Assistant Examiner*—Charles L. Patterson, Jr.
*Attorney, Agent, or Firm*—Gregory D. Williams; David G. Conlin

[57] ABSTRACT

The present invention is directed to a method for cloning and producing the FokI restriction endonuclease by (1) introducing the restriction endonuclease gene from *Flavobacterium okeanokoites* IFO 12536 into a host whereby the restriction gene is expressed; (2) fermenting the host which contains the vector encoding and expressing the FokI restriction endonuclease, and (3) purifying the FokI restriction endonuclease from the fermented host which contains the vector encoding and expressing the FokI restriction endonuclease activity.

10 Claims, 3 Drawing Sheets

Lane 1: 1.2ug marker DNA
Lane 2: 7.5ul extract/ug DNA
Lane 3: 3.8 ul extract/ug DNA
Lane 4: 1.9ul extract/ug DNA
Lane 5: 0.9ul extract/ug DNA
Lane 6: 0.5 ul extract/ug DNA
Lane 7: DNA incubated 1hr at 37C without extract
Lane 8: DNA incubated 1hr on ice without extract

METHOD FOR PRODUCING THE FOKI RESTRICTION ENDONUCLEASE AND METHYLASE

BACKGROUND OF THE INVENTION

The present invention relates to clones for the FokI restriction endonuclease and modification methylase, and to the production of these enzymes from the clones.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Over one hundred different restriction endonucleases have been identified among many hundreds of bacterial species that have been examined to date.

Bacteria usually possess only a small number restriction endonucleases per species. The endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences (AT)GGCC(AT), PuGCGCPy and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecule and cleaving them each time that the recognition sequence occurs. The disintegration that results inactivates many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones (HhaII: Mann et al., Gene 3: 97-112, (1978); EcoRII: Kosykh et al., Molec. gen. Genet 178: 717-719, (1980); PstI: Walder et al., Proc. Nat. Acad. Sci. 78 1503-1507, (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., Nucl. Acid. Res. 12:3659-3676, 1984; PaeR7: Gingeras and Brooks, Proc. Natl. Acad. Sci. USA 80:402-406, 1983; Theriault and Roy, Gene 19:355-359 1982; PvuII: Blumenthal et al., J. Bacteriol. 164:501-509, 1985).

A third approach, and one that is being used to clone a growing number of systems, involves selecting for an active methylase gene referring to our Pat. application No.: 707079 (BsuRI: Kiss et al., Nucl. Acid. Res. 13:6403-6421, 1985). Since restriction and modification genes tend to be closely linked, clones containing both genes can often be isolated by selecting for just the one gene. Selection for methylation activity does not always yield a complete restriction-modification system however, but instead sometimes yields only the methylase gene (BspRI: Szomolanyi et al., Gene 10:219-225, (1980); BcnI: Janulaitis et al, Gene 20: 197-204 (1982); BsuRI: Kiss and Baldauf, Gene 21: 111-119, (1983); and MspI: Walder et al., J. Biol. Chem. 258:1235-1241, (1983)).

A potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease. Another obstacle to cloning restriction-modification systems lies in the discovery that some strains of *E. coli* react adversely to cytosine modification; they possess systems that destroy DNA containing methylated cytosine (Raleigh and Wilson, Proc. Natl. Acad. Sci., USA 83:9070-9074, 1986). Cytosine-specific methylase genes cannot be cloned easily into these strains, either on their own, or together with their corresponding endonuclease genes. To avoid this problem it is necessary to use mutant strains of *E. coli* (McrA− and McrB−) in which these systems are defective.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

In accordance with the present invention there is provided a clone containing the genes for the FokI restriction endonuclease and modification methylase derived from *Flavobacterium okeanokoites* (IFO 12536), as well as related methods for the production of the enzymes. More specifically, this invention relates to clones which express the restriction endonuclease FokI, an enzyme which recognizes the DNA sequence GGATG and cleaves at 9/13 nucleotides downstream. See Sugisaki, H. and Kanazawa, S. 1981, Gene 16: 73-78, the disclosure of which is hereby incorporated by reference herein. FokI restriction endonuclease produced in accordance with the present invention is substantially pure and free of the contaminants normally found in FokI preparations made by conventional techniques, such as that disclosed by Sugisaki and Kanazawa, supra.

The preferred method for cloning this enzyme comprises forming a library containing the DNA from *Flavobacterium okeanokoites* (IFO 12536), isolating those clones which contain DNA coding for the FokI modification methylase and screening among these to identify those that also contain the FokI restriction endonuclease gene.

DETAILED DESCRIPTION OF THE INVENTION

The present invention relates to clones of the FokI restriction and modification genes, as well to the restriction endonuclease FokI produced from such clones. The FokI genes are cloned by a method which takes advantage of the fact that certain clones which are selected on the basis of containing and expressing the FokI modification methylase gene also contain the FokI restriction gene. The DNA of such clones is resistant to digestion, by the FokI restriction endonuclease. This resistance to digestion affords a means for selectively isolating clones encoding the FokI methylase and restriction endonuclease.

Figure 1:
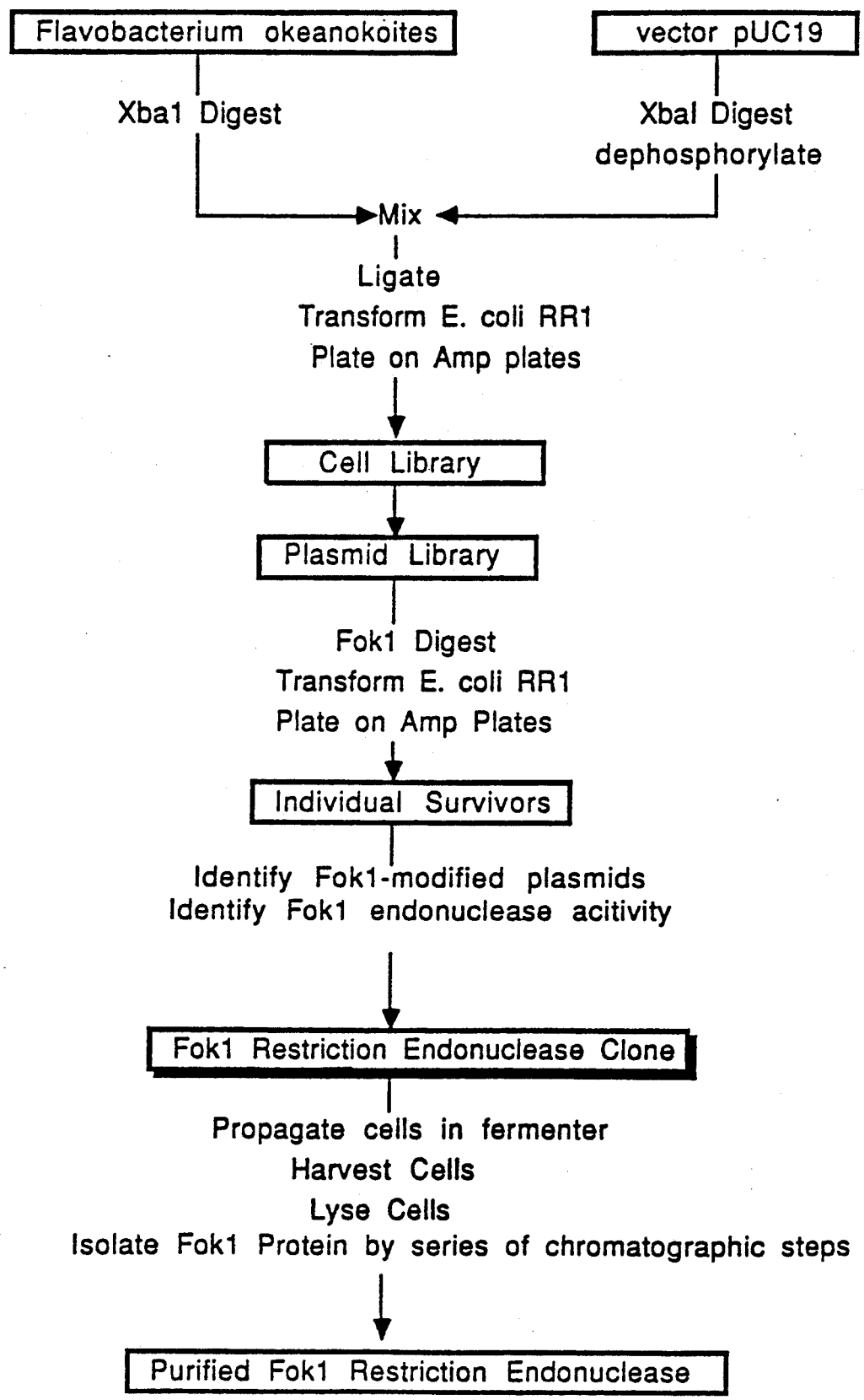
FIG. 1 illustrates the scheme for cloning and producing the FokI restriction endonuclease.

The method described herein by which the FokI restriction gene and methylase gene are preferably cloned and expressed are illustrated in FIG. 1, and they include the following steps:

1. The DNA of *Flavobacterium okeanokoites* is purified. *Flavobacterium okeanokoites* has been described in a number of publications including Sugisaki and Kanazawa, the disclosure of which is hereby incorporated by reference. Samples of this bacterium are available from the Institute for Fermentation, Osaka (IFO 12536).

2. The DNA is digested with the restriction endonuclease XbaI.

3. The digested DNA is ligated to a cloning vector such as pUC19 (ATCC 37254) that contains one or more FokI sites. The ligated DNA is transformed into an appropriate host such as *E. coli* strain RRI (ATCC 31343).

4. The DNA/cell mixture is plated onto antibiotic media selective for transformed cells, such as ampicillin. After incubation, the transformed cell colonies are collected together into a single culture, the cell library.

5. The recombinant plasmids are purified in toto from the cell library to make the plasmid library.

6. The plasmid library is digested to completion with the FokI restriction endonuclease, prepared from *Flavobacterium okeanokoites* by a method similar to that described in Sugisaki and Kanazawa, supra. FokI digestion differentially destroys unmodified, non-methylase-containing, clones, increasing the relative frequency of FokI methylase-carrying clones.

7. The digested plasmid library DNA is transformed back into an appropriate host such as *E. coli* strain RRI, and transformed colonies are again obtained by plating on antibiotic plates. The colonies are picked and their DNA is analyzed for the presence of the FokI modification gene in the following manner: The plasmid DNA that they carry is purified and incubated in vitro with FokI restriction endonuclease to determine whether it is resistant to digestion by FokI. The total cellular DNA (chromosomal and plasmid) of the clone is also purified and incubated with FokI restriction endonuclease. The DNA of clones that carry the FokI methylase gene should be fully modified, and both the plasmid DNA and the total DNA should be found to be substantially, or completely resistant to digestion.

8. Clones carrying the FokI restriction endonuclease are identified by preparing crude extracts of those clones identified in step 8 as carrying the FokI methylase gene, and assaying the extracts for FokI restriction endonuclease activity. Detection of the FokI restriction endonuclease activity in crude cell extracts is enhanced if the extracts are prepared from an *endo*A− strain of *E. coli*, such as MM294 (ATCC 33625), into which the plasmids have been transferred by transformation.

9. The FokI restriction endonuclease may be produced from clones carrying the FokI restriction and modification genes by propagation in a fermenter in a rich medium containing ampicillin. The cells are thereafter harvested by centrifugation and disrupted by sonication to produce a crude cell extract containing the FokI restriction endonuclease activity.

10. The crude cell extract containing the FokI restriction endonuclease activity is purified by standard protein purification techniques such as affinity-chromatography and ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE

Cloning of FokI Restriction Endonuclease Gene

1. DNA purification: 10 g of frozen *Flavobacterium okeanokoites* (IFO 12536) cells were thawed on ice for 1 hour then resuspended in 20 ml of 25% sucrose, 50mM Tris pH 8.0. 10 ml of 0.25M EDTA pH 8.0, and 6 ml of 10 mg/ml lysozyme in 0.25M Tris pH 8.0 were added. The suspension was kept on ice for 2 hours, then lysed by the addition of 24 ml of 1% Triton X-100, 50mM Tris pH 8.0, 67mM EDTA and 5 ml of 10% SDS. The solution was extracted with 70 ml of phenol, (previously equilibrated with 0.5M Tris pH 8.0), and 60 ml of Chloroform. The emulsion was centrifuged at 10K rpm for 30 minutes and the viscous upper layer was withdrawn and dialyzed against four changes of 10mM Tris pH 8.0, 1mM EDTA. The dialyzed solution was then digested with RNase at a final concentration of 100 ug/ml for 1 hour at 37° C. The DNA was then precipitated by adding NaCl to a final concentration of 0.4M, overlaying with 0.55 volumes of isopropyl alcohol, and spooling the DNA onto a glass rod by mixing the phases together. The DNA was resuspended in 10mM Tris pH 8.0, 1mM EDTA and stored at 4° C.

2. Digestion of DNA: The DNA was diluted to a concentration of 100 ug/ml in 50mM Tris pH 7.5, 50mM NaCl, 10mM MgCl$_2$, and 2 units of XbaI per ug of DNA were added. The solution was incubated at 37° C. for 1 hr, then digestion was terminated by heating to 72° C. for 12 minutes.

3. Ligation and transformation: 4.0 ug of XbaI-digested *Flavobacterium okeanokoites* DNA (40 ul) was mixed with 2.0 ug of XbaI-cleaved and dephosphorylated pUC19 (10 ul). 10 ul of 500mM Tris pH 7.5, 100mM MgCl$_2$, 100mM DTT, 5mM ATP, and 40 ul of sterile distilled water were added to bring the volume to 100 ul. 3.75 ul of T4 DNA ligase was added and the solution was incubated at 16° C. for 4 hours, then sterilized by extraction with 20 ul of chloroform. 80 ul of the ligated mixture was mixed with 1.0 ml of 50mM NaCl, 5mM Na$_3$ Citrate, 67mM CaCl$_2$ and 2.0 ml of ice-cold, competent *E. coli* RR1 (ATCC 31343) cells were added. The solution was incubated at 42° C. for 5 mins, then 8 ml of Luria-broth (L-broth) was added and incubation was continued at 30° C. for 4 hours.

4. Cell Library: The transformed cell culture was briefly centrifuged, the supernatant was discarded and the cells were resuspended in 1.0 ml of L-broth. 200 ul portions were plated onto Luria-agar (L-agar) plates containing 100 ug/ml ampicillin. After overnight incubation at 30° C., the plates were each flooded with 2.5 ml of 10mM Tris pH 7.5, 10mM MgCl$_2$ and the transformed colonies were scraped together and pooled.

5. Plasmid Library: 2.5 ml of the cell library was inoculated into 500 ml of L-broth containing 100 ug/ml ampicillin. The culture was shaken overnight at 30° C. then centrifuged at 4000 rpm for 5 minutes. The supernatant was discarded and the cell pellet was resuspended in 10 ml of 25% sucrose, 50mM Tris pH 8.0, at room temperature. 5 ml of 0.25M EDTA, pH 8.0, and 3 ml of 10 mg/ml lysozyme in 0.25M Tris, pH 8.0 were added. The solution was left on ice for 1 hour, then 12 ml of 1% Triton X-100, 50mM Tris pH 8.0, 67mM EDTA was forcefully pipetted in, and the suspension was gently swirled to achieve lysis.

The lysed mixture was transferred to a 50 ml tube and centrifuged for 45 min. at 17000 rpm, 4° C. The supernatant was removed with a pipette. 20.0 gm of solid CsCl was weighed into a 50 ml plastic screw-cap tube and 22.0 gm of supernatant was pipetted into the tube and mixed. 1.0 ml of 5 mg/ml ethidium bromide in 10mM Tris pH 8.0, 100mM NaCl, 1mM EDTA was added. The solution was transferred to two ⅜ in. × 3 in. centrifuge tubes and spun in a Beckman Ti70 rotor for 42 hours at 44000 rpm, 17° C. To collect the plasmids, the tubes were opened, illuminated with ultraviolet light, and the lower of the two fluorescent bands was collected by syringe. The lower band from each tube was combined and the ethidium bromide was removed by extracting four times with an equal volume of water-saturated, ice-cold N-Butanol.

The extracted solution was dialyzed against 4 changes of 10mM Tris pH 7.5, 1mM EDTA, then the nucleic acid was precipitated by the addition of 2 vols. of isopropanol and sufficient 5M NaCl to reach a final concentration of 0.4M. The solution was stored overnight at −20° C. then centrifuged for 15 min. at 15000 rpm, 0° C. The supernatant was discarded, the pellet was air-dried for 15 min. then dissolved in 500 ul of 10mM Tris pH 7.5, 1mM EDTA and stored at −20° C. The plasmid DNA concentration was found to be approximately 150 ug/ml.

6. Digestion of the Plasmid Library: The plasmid library was diluted to 30 ug/ml in 10mM Tris pH 7.5, 10mM MgCl$_2$, 6mM mercaptoethanol, 20mM KCl. FokI restriction endonuclease was added to a concentration of 16 units/ug DNA, and the tube was incubated at 37° C. for 1 hour. The reaction was terminated by heating to 72° C. for 12 minutes.

7. Transformation: 12.5 ul of the digested library was transformed into *E. coli* strain RRI, plated onto Lagar containing 100 ug/ml ampicillin and incubated overnight at 30° C. FokI digestion reduced the number of transformants by a factor of $10^3$ compared to transformation with undigested plasmids. Fourteen colonies were picked from the survivors on the plates and each was inoculated into 10 ml of L-broth containing ampicillin, to prepare a miniculture, and streaked onto an L-agar plate containing ampicillin, to prepare a master stock.

8. Analysis of surviving individuals: fourteen of the surviving colonies obtained from section 7 were grown into 10 ml cultures and the plasmids that they carried were prepared by the following miniprep purification procedure, adapted from the method of Birnboim and Doly, *Nucleic Acids Res.* 7: 1513 (1979).

Miniprep Procedure: Each culture was centrifuged at 8000 rpm for 5 minutes; the supernatant was discarded and the cell pellet was resuspended in 1.0 ml of 25mM Tris, 10mM EDTA, 50mM glucose, pH 8.0, containing 1 mg/ml lysozyme. After 10 minutes at room temperature, 2.0 ml of 0.2M NaOH, 1% SDS was added to each tube and the tubes were shaken to lyse the cells, then placed on ice. Once the solutions had cleared, 1.5 ml of 3M sodium acetate, pH 4.8, was added to each and shaken. The precipitates that formed were spun down at 15000 rpm, 4° C. for 10 minutes. Each supernatant was poured into a centrifuge tube containing 3 ml of isopropanol and mixed. After 10 minutes at room temperature, the tubes were spun at 15000 rpm for 10 minutes to pellet the precipitated nucleic acids. The supernatants were discarded and the pellets were air-dried at room temperature for 30 minutes. Once dry, the pellets were resuspended in 850 ul of 10mM Tris, 1mM EDTA, pH 8.0. 75 ul of 5M NaCl was added to each and the solutions were transferred to Eppendorf tubes containing 575 ul of isopropanol, and again precipitated for 10 minutes at room temperature. The tubes were then spun for 45 seconds in a microfuge, the supernatants were discarded and the pellets were air-dried. The pellets were then dissolved in 500 ul of 10mM Tris, 1mM EDTA, pH 8.0, containing 100 ug/ml RNase and incubated for 1 hour at 37° C. to digest the RNA. The DNA was precipitated once more by the addition of 50 ul of 5M NaCl followed by 350 ul of isopropanol. After 10 minutes at room temperature, the DNA was spun down by centrifugation for 45 seconds, the supernatants were discarded and the pellets were redissolved in 150 ul of 10mM Tris 1mM EDTA, pH 8.0. The plasmid minipreps were subsequently analyzed by digestion with FokI and XbaI.

Figure 2:
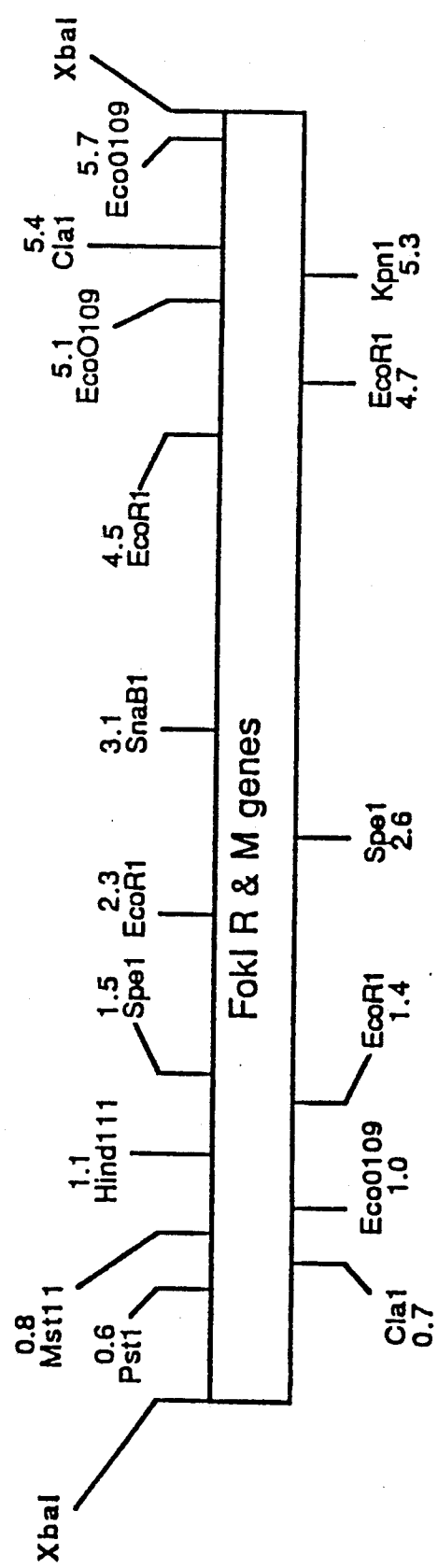
FIG. 2 is a restriction map of a 6 kb XbaI fragment of *F.okeanokoites* DNA that encodes the FokI restriction endonuclease and modification methylase. The fragment was cloned into the XbaI site of pUC19 (ATCC 37254) to create pML109RM 119-1.

9. FokI Methylase Gene Clones: Eleven of the plasmids that were analyzed were found to be sensitive to FokI and to carry random XbaI fragments of *Flavobacterium okeanokoites* DNA. These plasmids were spurious survivors, and were discarded. The three remaining plasmids were found to be resistant to FokI and to carry a single XbaI fragment 6kb in length. (FIG. 2). These plasmids appeared to be identical; one of them, pML109RM 119-1 was analyzed further and was shown to carry not only the FokI modification methylase gene but also the FokI restriction endonuclease gene.

10. FokI Restriction Gene Clone: pML109RM 119-1 was found to carry the FokI restriction endonuclease gene by assaying an extract prepared from *E. coli* strain MM294 (ATCC 33629) into which the plasmid had been transferred by transformation. A sample of pML109RM119-1 in MM294 has been deposited at the American Type Culture Collection under ATCC Accession No. 40898.

Endonuclease Assay: To assay for FokI endonuclease activity, two solutions were prepared:

(i) 10×restriction endonuclease buffer: 100mM Tris, pH 7.5, 100mM MgCl$_2$, 60mM mercaptoethanol, 200mM KCl.

(ii) digestion reaction mix: 18 ul lambda DNA (630 ug/ml), 56 ul 10×restriction endonuclease buffer, 486 ul distilled water.

Figure 3:
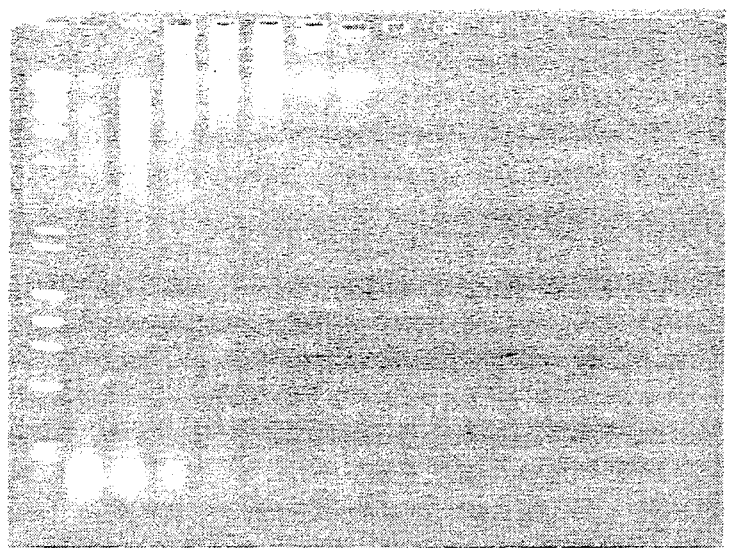
FIG. 3 is a photograph of an agarose gel illustrating FokI restriction endonuclease activity in a cell extract of *E. coli* MM294 (ATCC 33625) carrying pML109RM 119-1.

The cell extract was prepared as follows: A 50 ml culture was grown overnight in L-broth plus 100 ug/ml ampicillin at 30° C. The cells were pelleted by centrifugation at 4000 rpm for 5 minutes then resuspended in 4 ml 10mM KPO$_4$ pH 7.5, 10mM mercaptoethanol, 0.1mM EDTA. 0.5 ml of 1.8 mg/ml lysozyme in the same buffer was added and the suspension was left on ice for 1 hour. 1 ml of the suspension was sonicated gently for three 10-second bursts to disrupt the cells. The tube was spun for 10 minutes in a microfuge and the supernatant was used as the cell extract. To assay the extract, the digestion reaction mix was dispensed into 5 tubes, 100 ul into the first tube and 50 ul into each of the remaining 4 tubes. 15 ul of the extract was added to the first tube and mixed. 50 ul was removed from the first tube and transferred to the second tube, mixed and so on. The first tube thus received 7.5 ul of extract per ug of DNA, the second tube 3.75 ul/ug, the third tube, 1.88 ul/ug and so on. The tubes, each now containing 50 ul, were incubated at 37° C. for one hour, then a 20 ul sample of each was analyzed by gel electrophoresis. The extract was found to contain approximately 100 units of FokI endonuclease per ml, which corresponds to about 1500 units per gram of cells. (FIG. 3)

What is claimed is:

1. Isolated DNA coding for the FokI restriction endonuclease, wherein the isolated DNA is obtainable from the vector pML109RM119-1.

2. A recombinant DNA vector comprising a vector into which a DNA segment coding for the FokI endonuclease produced by *Flavobacterium okeanokoites* IFO 12536 has been inserted.

3. Isolated DNA coding for the FokI restriction endonuclease and methylase, wherein the isolated DNA is obtainable from the vector pML109RM119-1.

4. A cloning vector which comprises the isolated DNA of claim 1.

5. A cloning vector which comprises the isolated DNA of claim 3.

6. The cloning vector of claim 5, wherein the cloning vector comprises pML109RM119-1.

7. A host cell transformed by the vector of claim 4, 5 or 6.

8. A method of cloning DNA coding for an FokI restriction endonuclease comprising:
   (a) purifying DNA from *Flavobacterium okeanokoites* IFO 12536;
   (b) digesting the purified DNA with XbaI to form DNA fragments;
   (c) ligating the DNA fragments into pUC19;
   (d) transforming a host cell with the cloning vector of step (c) to form a cell library;
   (e) purifying recombinant vectors from the cell library to form a plasmid library;
   (f) contacting the plasmid library of step (e) with FokI to form a digestion pool, transforming the digestion pool into a host cell, and screening for the presence of one or more cloning vectors containing DNA coding for an FokI methylase;
   (g) transferring the cloning vector of step (f) which contains DNA coding for FokI methylase into *E. coli* MM294 and screening for the presence of DNA coding for an FokI restriction endonuclease; and
   (h) isolating the cloning vector of step (g) which contains DNA coding for FokI restriction endonuclease.

9. A method producing FokI restriction endonuclease comprising culturing a host cell transformed with the vector of claim 4, 5 or 6 under conditions suitable for the expression of said endonuclease.

10. A method of producing FokI restriction endonuclease:
   (a) purifying DNA from *Flavobacterium okeanokoites* IFO 12536;
   (b) digesting the purified DNA with XbaI to form DNA fragments;
   (c) ligating the DNA fragments into pUC19;
   (d) transforming a host cell with the cloning vector of step (c) to form a cell library;
   (e) purifying recombinant vectors from the cell library to form a plasmid library;
   (f) contacting the plasmid library of step (e) with FokI to form a digestion pool, transforming the digestion pool into a host cell, and screening for the presence of one or more cloning vectors containing DNA coding for a FokI methylase;

(g) transferring the cloning vector of step (f) which contains DNA coding for FokI methylase into *E. coli* MM294 and screening for the presence of DNA coding for an FokI restriction endonuclease;

(h) isolating the cloning vector of step (g) which contains DNA coding for FokI restriction endonuclease; and (i) culturing a host cell transformed with the cloning vector of step (h) under conditions suitable for expression of FokI restriction endonuclease.

* * * * *